(12) United States Patent
Corma Canos et al.

(10) Patent No.: US 10,538,469 B2
(45) Date of Patent: Jan. 21, 2020

(54) METHOD FOR PRODUCING 1-OCTANOL (71) Applicant: ABENGOA BIOENERGIA NUEVAS TECNOLOGIAS, S.A., Seville (ES)

(72) Inventors: Avelino Corma Canos, Valencia (ES); Marcelo Eduardo Domine, Valencia (ES); Juan Luis Sanz Yague, Seville (ES); Francisco Antonio Ladron De Guevara Vidal, Seville (ES)

(73) Assignee: ABENGOA BIOENERGIA NUEVAS TECNOLOGIAS, S.A. (ES)

( * ) Notice: Subject to any disclaimer, the term of this patent is extended or adjusted under 35 U.S.C. 154(b) by 0 days.

(21) Appl. No.: 16/303,387

(22) PCT Filed: May 26, 2017

(86) PCT No.: PCT/ES2017/070357
§ 371 (c)(1),
(2) Date: Nov. 20, 2018

(87) PCT Pub. No.: WO2017/203089
PCT Pub. Date: Nov. 30, 2017

(65) Prior Publication Data
US 2019/0300463 A1    Oct. 3, 2019

(30) Foreign Application Priority Data

May 26, 2016   (ES) .................... 201630680

(51) Int. Cl.
*C07C 29/34* (2006.01)
*B01J 21/10* (2006.01)
(Continued)

(52) U.S. Cl.
CPC .............. *C07C 29/34* (2013.01); *B01J 21/02* (2013.01); *B01J 21/10* (2013.01); *B01J 23/892* (2013.01);
(Continued)

(58) Field of Classification Search
CPC .. C07C 29/34; B01J 21/02; B01J 21/10; B01J 23/89; B01J 23/892; B01J 23/8926;
(Continued)

(56) References Cited

U.S. PATENT DOCUMENTS 8,071,822 B2 * 12/2011 Ozer ....................... C07C 29/34
568/902
2010/0160693 A1   6/2010 Kourtakis et al.
2015/0166443 A1 * 6/2015 Arjona Antolin ....... C07C 29/34
568/902.2

FOREIGN PATENT DOCUMENTS

CN    101530802 A    9/2009
EP    2679303 A1     1/2014
(Continued)

OTHER PUBLICATIONS

ES 2570231, Sanz Yague, J.L. et al., Process for the preparation of higher alcohols form ethanol and n-hexanol by Guerbet condensation, May 17, 2016, English translation, 77 pages (Year: 2016).*
(Continued)

*Primary Examiner* — Yate' K Cutliff
(74) *Attorney, Agent, or Firm* — Hayes Soloway PC (57) ABSTRACT

The present invention relates to a method for producing 1-octanol comprising a contact step between ethanol, n-hexanol and two catalysts A and B, wherein catalyst A comprises a metal oxide comprising Ga and a noble metal and catalyst B comprises a metal oxide comprising Cu, Ni or any mixture thereof.

26 Claims, 3 Drawing Sheets

(51) Int. Cl.
*B01J 21/02* (2006.01)
*B01J 23/89* (2006.01)
*C07C 31/125* (2006.01)

(52) U.S. Cl.
CPC ......... *B01J 23/896* (2013.01); *B01J 23/8926* (2013.01); *B01J 23/8946* (2013.01); *B01J 23/8906* (2013.01); *B01J 23/8953* (2013.01); *B01J 23/8986* (2013.01); *C07C 31/125* (2013.01)

(58) Field of Classification Search
CPC .. B01J 23/8946; B01J 23/896; B01J 23/8993; B01J 23/8986; B01J 23/8953; B01J 23/8906
See application file for complete search history.

(56) References Cited

FOREIGN PATENT DOCUMENTS

| | | | |
|---|---|---|---|
| EP | 2679304 | A1 | 1/2014 |
| ES | 2570231 | * | 5/2016 ............ C07C 29/34 |
| ES | 2570231 | A2 | 5/2016 |
| ES | 2570233 | A1 | 5/2016 |
| WO | 2009026510 | A1 | 2/2009 |
| WO | 2009097310 | A1 | 8/2009 |
| WO | 2009097312 | A1 | 8/2009 |
| WO | 2014001595 | A1 | 1/2014 |
| WO | 2016075353 | A1 | 5/2016 |

OTHER PUBLICATIONS

Cosimo et al., "Structure and Surface and Catalytic Properties of Mg—Al Basic Oxides"; Journal of Catalysis; 1998; p. 499-510; 178; Academic Press.

Carlini et al.;"Selective synthesis of isobutanol by means of the Guerbet reaction Part 3: Methanolin-propanol condensation by using bifunctional catalytic systems based on nickel, rhodium and ruthenium species with basic components"; Journal of Molecular Catalysis; 2003; p. 409-418; 206; Elsevier B.V.

* cited by examiner

METHOD FOR PRODUCING 1-OCTANOL

The present invention relates to a method for producing 1-octanol using two catalysts A and B, catalyst A, metal oxide-type comprising a noble metal and gallium, and a catalyst B, metal oxide-type comprising Cu, Ni or any mixture thereof. Therefore, the present invention belongs to the field of catalytic methods for producing higher alcohols.

STATE OF THE ART

In recent years, numerous scientific publications and patents have been published on the use of hydrotalcite-type materials as catalysts in alcohol condensation reactions, such as the Guerbet reaction, both in batch systems and in continuous fixed bed reactors. Most of the reactions described with said catalyst relate to the production of n-butanol from ethanol. The studies performed with these mixed Mg—Al oxides revealed that the catalytic activity of these materials depends on the nature, density and resistance of the basic surface sites which, in turn, depend on the molar Mg/Al composition in the solid (J. I. Di Cosimo, V. K. Diez, M. Xu, E. Iglesia, C. R. Apesteguia, *J. Catal.* 178, 499-510, 1998).

More recently, it has also been established that the mixed oxides derived from Cu/Mg/Al-based hydrotalcite show better catalytic activities in alcohol condensation that other analogous hydrotalcites, such as those including supported Ni species (C. Carlini, A. Macinai, M. Marchionna, M. Noviello, A. M. R. Galletti, G. Sbrana, *J. Mol. Catal. A: Chem.* 206, 409, 2003; X. Jiang, Z. Du, document CN101530802. 2009), among others.

Furthermore, international application WO2009026510 discloses a method for synthesising n-butanol by means of a material derived from the thermal decomposition of a hydrotalcite which preferably comprises magnesium and aluminium. Likewise, documents WO2009097312, US20100160693 and WO2009097310 disclose materials produced by the thermal decomposition of hydrotalcites modified by the inclusion of metal carbonates and ethylenediaminetetraacetates, which have been developed by DU PONT as catalysts in alcohol condensation reactions which operate in a fixed bed at 300° C. and atmospheric pressure. The best results under these conditions have been achieved with a material derived from Cu—Mg—Al-based hydrotalcite (containing OH⁻ as the anion), which has high ethanol conversion (≈44%) with moderate selectivities (≈44%) to n-butanol. When these same materials were assayed in the catalytic conversion of ethanol into n-butanol in the presence of hydrogen in the reaction system, the n-butanol yields obtained were significantly lower in all cases.

The synthesis of high molecular weight alcohols (containing between 8-16 carbon atoms) has been of interest in recent years due to the potential of these oxygenated compounds for their use as surfactants and for the addition to polymers, lubricants, cosmetics and many other specific uses. In particular, n-hexanol (n-HexOH), with an annual production of 450,000 kilograms, with a low market value based on small-scale supply to laboratories, can be transformed into more valuable 1-octanol (1-OctOH) or 1-decanol (n-DeOH).

1-OctOH and n-DeOH, with a worldwide production that exceeds 400,000 tons per year, are mainly used as surfactants and for addition to polymers, lubricants, cosmetics and many other specific uses.

Currently, n-HexOH, produced as unwanted by-product, is normally used to reduce the fuel load in ovens or similar methods. However, increasing the value of n-HexOH by means of conversion to higher alcohols such as 1-OctOH and DeOH would help to improve the economy of the methods in question.

1-octanol may be naturally produced, from grease, oils and waxes of animal or plant origin, in addition to synthetically, from petrochemical products such as olefins and paraffins.

The development of catalysts has been of great importance for improving synthesis methods of 1-octanol, allowing an increase in yields and a reduction in reaction times, and consequently, reduction in the costs of these industrial methods. Patent applications EP2679304A1 and EP2679303A1 disclose a method for producing a catalyst of metal oxide-type comprising gallium and a noble metal for the method of converting $C_1$-$C_3$ alcohols into higher alcohols (specifically, methanol, ethanol, propanol or isopropanol into n-butanol) which increases the selectivity of the reaction to n-butanol and the productivity of n-butanol. Application WO2016075353 relates to a metal oxide-type catalyst comprising gallium or gallium and vanadium for producing 1-octanol.

It has been discovered that precisely this type of catalyst, used together with a metal oxide-type catalyst comprising Ni, Cu or any mixture thereof, leads to the production of higher alcohols, mainly 1-octanol, when it comes into contact with ethanol and n-hexanol.

DESCRIPTION OF THE INVENTION

The present invention relates to a method for producing 1-octanol from ethanol and n-hexanol in the presence of two catalysts A and B, two catalysts based on metal oxide wherein A comprises Ga and a noble metal and wherein B comprises Ni, Cu or any mixture thereof. Likewise, the present invention also relates to the use of said catalysts for producing octanol.

The invention has the following advantages with respect to the state of the art:
- the yield of higher alcohols is greater when the two catalysts A and B are used, in comparison with the use of said catalysts separately,
- they are more selective towards the production of linear alcohols and reduce the quantity of branched alcohols;
- only catalyst A requires a noble metal, which means a saving in the necessary quantity of these metals;
- it will require less catalyst mass in an industrial application to produce the same quantity of linear alcohols;
- high yields of higher alcohols working at temperatures ≤250° C. and pressures below 40 bar, even in absence of $H_2$.

Therefore, a first aspect of the present invention relates to a method for producing 1-octanol comprising a contact step between ethanol, n-hexanol and two catalysts A and B, wherein catalyst A comprises:

i) a metal oxide comprising the following metals:
M1 is a divalent metal selected from Mg, Zn, Cu, Co, Mn, Fe, Ni, Ca and any mixture thereof, preferably M1 is a divalent metal selected from Mg, Ca and any mixture thereof, more preferably M1 is Mg.
M2 is Trivalent Ga; and
ii) a noble metal selected from Pd, Pt, Ru, Rh, Re and any mixture thereof;
and catalyst B comprises a metal oxide comprising the following metals:
M3 is a divalent metal selected from Mg, Zn, Cu Co, Mn, Fe, Ni, Ca and any mixture thereof, M4 is a trivalent metal selected from Al, La, Fe, Cr, Mn, Co, Ni and any mixture thereof, with the condition that catalyst B comprises at least Cu, Ni or any combination thereof, wherein the Ni comprises divalent or trivalent Ni or any mixture thereof.

"Divalent metal" or "trivalent metal" is understood to mean a metal cation with a +2 or +3 charge, respectively.

Catalysts A and B can be physically mixed prior to their contact with ethanol and n-hexanol.

In an embodiment of the first aspect of the present invention, the metal oxide of catalyst A further comprises an M5 metal, wherein M5 is at least one trivalent metal selected from Al, La, Fe, Cr, Mn, Co and Ni, preferably M5 comprises Al, more preferably M5 is Al.

In another embodiment of the first aspect of the present invention, catalyst A is produced by means of a method comprising the following steps:

a) total or partial thermal decomposition of a hydrotalcite $HT_A$ with the formula $$[M1_{1-(x+y)}M2_yM5_x(OH)_2][Q_A^{m-}{}_{(x+y)/m} \cdot nH_2O],$$
wherein:

M1, M2 and M5 have been previously defined, $Q_A$ is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II), x is a value between 0 and 0.5; y is a value between 0.00001 and 0.49; m is an integer between 1 and 4; and n is greater than 0, preferably n is a value between 1 and 100, and more preferably between 1 and 20;

b) addition to the metal oxide produced in step a) of:

a noble metal selected from Pd, Pt, Ru, Rh, Re and any mixture thereof.

n indicates the number of crystallisation water molecules and depends on the hydrotalcite cation composition.

"Hydrotalcite" is understood to mean the structural family of laminar mixed hydroxides with the formula described above. The general structure of hydrotalcites is very well known to persons skilled in the art.

The term "thermal decomposition" is understood to mean a chemical decomposition or structural change produced by the action of heat. This decomposition may be total or partial, depending on whether said decomposition is performed completely or, in contrast, it is performed partially. This thermal decomposition may be performed at temperatures greater than 150° C. and in the presence of an oxidising or non-oxidising gas.

The combination of a catalyst A and a catalyst B provide greater yields of 1-octanol in a nitrogen atmosphere than if only a catalyst A or a catalyst B was used. In other words, there is a synergy in the combined use of the two catalysts.

With respect to the anion, $Q_A$ is preferably at least one anion selected from the list comprising $CO_3^{2-}$, $HCO_3^-$, $O_2^-$, $OH^-$, $Cl^-$, $NO_3^{2-}$, $Cl^-$, $F^-$, $Br^-$, $I^-$, $ClO_4^-$, $CH_3COO^-$, $C_6H_5COO^-$ and $SO_4^{2-}$; even more preferably, $CO_3^{2-}$, $HCO_3^{2-}$, $O_2^-$ and $OH^-$.

In another embodiment of the first aspect of the present invention, the hydrotalcite $HT_A$ is produced by the co-precipitation of M1, M2 and M5 compounds.

In another embodiment of the first aspect of the present invention, M1 is a divalent metal selected from Mg, Ca and any mixture thereof, preferably M1 is Mg.

Preferably, the co-precipitation is performed in aqueous phase. The co-precipitation of the compounds may be preferably performed after the addition of a solution of at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II) to a solution of at least one compound of M1, at least one compound of M2 and at least one compound of M5. This anion may be introduced between the layers of the resulting hydrotalcite. Sodium and/or potassium salts thereof may be used in order to produce solutions of the anion. Preferably, the at least one anion is selected from carbonate, bicarbonate and hydroxide. The best results are produced when the co-precipitation is performed at a pH higher than 7, preferably between 10 and 14. Furthermore, with the aim of regulating the pH, preferably sodium and/or potassium hydroxide are used.

Preferably, prior to the precipitation of said compounds, there is dissolution of at least one compound of M1, at least one compound of M2 and at least one compound of M5. Soluble M1, M2 and M5 compounds are understood to mean any salt which, when placed in contact with a solvent, dissociates, preferably in a polar solvent, more preferably water. Examples of soluble M1, M2 and M5 compounds may be nitrates, halides, sulfates, carboxylates and, in general, oxoacids comprising M1, M2 or M5; preferably, the soluble M1, M2 and M5 compounds are nitrates.

In another embodiment of the first aspect of the present invention, catalyst B is produced by means of a method comprising a step of total or partial thermal decomposition of a hydrotalcite $HT_B$ with the formula:

$$[M3_{(1-z)}M4_z(OH)_2][Q_B^{p-}{}_{(z/n)} \cdot rH_2O],$$ wherein:

M3 and M4 have been previously defined, $Q_B$ is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II), z is a value higher than 0 and lower than 1, preferably z is a value between 0.1 and 0.8; p is an integer between 1 and 4; and r is higher than 0, preferably r is a value between 1 and 100, and more preferably between 1 and 20.

With respect to the anion, $Q_B$ is preferably at least one anion selected from the list comprising $CO_3^{2-}$, $HCO_3^-$, $O_2^-$, $OH^-$, $Cl^-$, $NO_3^{2-}$, $Cl^-$, $F^-$, $Br^-$, $I^-$, $ClO_4^-$, $CH_3COO^-$, $O_6H_5COO^-$ and $SO_4^{2-}$; even more preferably, $CO_3^{2-}$, $HCO_3^-$, $O_2^-$ and $OH^-$.

In another embodiment of the first aspect of the present invention, the hydrotalcite $HT_B$ is produced by the co-precipitation of M3 and M4 compounds.

In another embodiment of the first aspect of the present invention, M3 is a divalent metal selected from Mg, Ca, Cu, Ni and any mixture thereof, preferably M3 is a divalent metal selected from Mg, Cu, Ni and any mixture thereof.

In another embodiment of the first aspect of the present invention, M4 is a trivalent metal selected from Al, Ni and any mixture thereof. More preferably M4 is Al.

In another embodiment of the first aspect of the present invention, catalyst B comprises Cu and Ni. The Ni may be both divalent and trivalent, preferably the Ni is divalent. Preferably, catalyst B comprises Mg, Al, Cu and Ni.

In another embodiment of the first aspect of the present invention, if catalyst B only has Ni, the concentration of Ni is between 0.1% and 10% by weight with respect to the total of catalyst B. In another embodiment of the first aspect of the present invention, if the catalyst only has Cu, the concentration of Cu is between 0.1% and 10% by weight with respect to the total weight of catalyst B. In another embodiment of the first aspect of the present invention, the sum of the concentrations of Cu and Ni is between 0.2% and 10% by weight with respect to the total of catalyst B. These percentages refer to a weight of Cu and/or Ni not by weight of equivalent oxides.

In an embodiment of the first aspect of the present invention, the molar ratio (Mg+Cu+Ni/Al) is between 1 and 6, preferably between 2 and 5.

Preferably, the co-precipitation is performed in aqueous phase. The co-precipitation of the compounds may be preferably performed after the addition of a solution of at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II) to a solution of at least one compound of M3 and at least one compound of M4. This anion may be introduced between the layers of the resulting hydrotalcite. Sodium and/or potassium salts thereof may be used in order to produce solutions of the anion. Preferably, the at least one anion is selected from carbonate, bicarbonate and hydroxide. The best results are produced when the co-precipitation is performed at a pH higher than 7, preferably between 10 and 14. Furthermore, with the aim of regulating the pH, preferably sodium and/or potassium hydroxide are used.

Preferably, prior to the precipitation of said compounds, there is dissolution of at least one compound of M3 and at least one compound of M4. Soluble M3 and M4 compounds are understood to mean any salt which, when placed in contact with a solvent, dissociates, preferably in a polar solvent, more preferably water. Examples of soluble M3 and M4 compounds may be nitrates, halides, sulfates, carboxylates and, in general, oxoacids comprising M3 or M4; preferably, the soluble M3 and M4 compounds are nitrates.

The gels resulting from the co-precipitation as described above are filtered, washed with water and adequately dried. The presence of a hydrotalcite-type structure may be corroborated by X-ray diffraction analysis (XRD), whilst the composition (quantity and type of constituent) of the hydrotalcites or the corresponding mixed oxides produced by thermal decomposition of the aforementioned hydrotalcites may be determined by means of inductively coupled plasma mass spectrometry (ICP-MS) and chemical analysis, among others.

In another embodiment of the first aspect of the present invention, the weight ratio of catalysts A and B is between 1:10 and 10:1, preferably is 1:5 to 5:1, and more preferably is 1:1.

In another embodiment of the first aspect of the present invention, the thermal decomposition of the hydrotalcites $HT_A$ and $HT_B$ is performed by means of calcination under atmosphere of oxygen, nitrogen or any mixture thereof at a temperature ranging between 250° C. and 650° C., preferably between 350° C. and 550° C. The thermal decomposition of the hydrotalcites is preferably performed during an interval of 0.5 to 48 hours, preferably between 1 and 24 hours. This method may be performed by heating the hydrotalcites in a gaseous atmosphere and may be performed in a static oven or a calcination reactor with a controlled gas flow, the latter being the preferred system. The gas may be an oxidising gas or a non-oxidising gas. Examples of oxidising gases may include air and oxygen. Examples of non-oxidising gases may be inert gases, such as nitrogen, argon, helium and reducing gases, such as, for example, carbon dioxide, hydrogen and ammonia. Preferably, the calcination is performed in the presence of oxygen, nitrogen or mixtures thereof, and, even more preferably, in the presence of oxygen and nitrogen.

In another embodiment of the first aspect of the present invention, the noble metal of catalyst A is added to the metal oxide by wet impregnation, incipient volume impregnation or deposition-precipitation, preferably the noble metal is added to the metal oxide by wet impregnation, incipient volume impregnation or deposition-precipitation, more preferably by incipient volume impregnation. The incipient volume impregnation method, also called incipient wetness impregnation method, is based on the use of a minimum quantity of liquid for the impregnation, only that which is necessary to reach the maximum saturation of the corresponding solid.

In another embodiment of the first aspect of the present invention, the noble metal of catalyst A comprises Pd, preferably the noble metal is Pd. The best yields for 1-octanol have been produced when the calcinated hydrotalcites containing Ga are impregnated with Pd.

In another embodiment of the first aspect of the present invention, the concentration of the noble metal in catalyst A ranges between 0.001% and 10% by weight with respect to the total catalyst A, preferably between 0.01% and 5%.

In another embodiment of the first aspect of the present invention, catalyst A is produced by means of a method comprising the following steps:

a) total or partial thermal decomposition of a hydrotalcite $HT_A$ with the formula $[M1_{1-(x+y)}M2_yM5_x(OH)_2][Q_A^{m-}{}_{(x+y)/m} \cdot nH_2O]$,
wherein:

M1, M2 and M5 have been previously defined, preferably M1 is Mg, M5 is Al;

$Q_A$ is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II), preferably, $CO_3^{2-}$, $HCO_3^-$, $O_2^-$ and $OH^-$;

x is a value between 0 and 0.5; y is a value between 0.00001 and 0.49; m is an integer between 1 and 4; and n is greater than 0, preferably n is a value between 1 and 100, and more preferably between 1 and 20;

b) addition to the metal oxide produced in step a) of:

a noble metal selected from Pd, Pt, Ru, Rh, Re and any mixture thereof, preferably Pd; and catalyst B is produced by means of a method comprising a step of total or partial thermal decomposition of a hydrotalcite $HT_B$ with the formula:

$[M3_{(1-z)}M4_z(OH)_2][Q_B^{p-}{}_{(z/n)} \cdot rH_2O]$, wherein:

M3 and M4 have been previously defined, preferably M3 is a divalent metal selected from Mg, Cu, Ni and any mixture thereof, M4 is a trivalent metal selected from Al, Ni and any mixture thereof;

$Q_B$ is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II), preferably, $CO_3^{2-}$, $HCO_3^-$, $O_2^-$ and $OH^-$; z is a value higher than 0 and lower than 1, preferably z is a value between 0.1 and 0.8; p is an integer between 1 and 4; and r is higher than 0, preferably r is a value between 1 and 100, and more preferably between 1 and 20.

With respect to the anion, $Q_B$ is preferably at least one anion selected from the list comprising $CO_3^{2-}$, $HCO_3^-$, $O_2^-$, $OH^-$, $Cl^-$, $NO_3^{2-}$, $Cl^-$, $F^-$, $Br^-$, $I^-$, $ClO_4^-$, $CH_3COO^-$, $C_6H_5COO^-$ and $SO_4^{2-}$; even more preferably, $CO_3^{2-}$, $HCO_3^-$, $O_2^-$ and $OH^-$.

In another embodiment of the first aspect of the present invention, there is a calcination step after the addition of the noble metal of catalyst A. This calcination is preferably calcination in an atmosphere of oxygen, nitrogen or any mixture thereof. This calcination is preferably performed at a temperature ranging between 250° C. and 650° C., and, even more preferably, between 350° C. and 550° C. This calcination is preferably performed during an interval ranging between 0.5 and 48 hours, preferably between 1 and 24 hours, and, even more preferably, between 1 and 6 hours. This method may be performed by heating the material derived from hydrotalcite $HT_A$ in a gaseous atmosphere and may be performed in a static oven or a calcination reactor with a controlled gas flow, the latter being the preferred system. The gas may be an oxidising gas or a non-oxidising gas. Examples of oxidising gases may include air and oxygen. Examples of non-oxidising gases may be inert gases, such as nitrogen, argon, helium and reducing gases, such as, for example, carbon dioxide, hydrogen and ammonia. Preferably, the calcination is performed in the presence of oxygen, nitrogen or mixtures thereof, and, even more preferably, in the presence of oxygen and nitrogen.

In another embodiment of the first aspect of the present invention, there is a calcination step after the addition of the noble metal of catalyst A and a reduction step subsequent to said calcination.

In a preferred embodiment of the first aspect of the present invention, the method of the invention as previously described further comprises a reduction step after the calcination subsequent to the addition of the noble metal of catalyst A.

In another preferred embodiment of the first aspect of the present invention, after the addition of the noble metal of catalyst A, there is a calcination step of catalysts A and B, and a reduction step subsequent to the calcination of catalysts A and B.

During the reduction, the noble metal, which acts as one of the main active sites in the method, is reduced. This reduction step is preferably performed in an $H_2$ atmosphere and, preferably, at a temperature ranging between 200° C. and 500° C., more preferably between 250° C. and 450° C. This reduction is preferably performed during an interval between 0.5 and 48 hours, preferably between 1 and 24 hours, and, even more preferably, between 1 and 6 hours. Preferably, the reduction may be performed in a step prior to the introduction of the catalyst in the catalytic reactor or may take place immediately prior to the contact step with the reagent, i.e. with ethanol and hexanol, with the same reactor.

In another preferred embodiment of the first aspect of the invention, the contact between ethanol, n-hexanol and catalysts A and B is performed in a reactor selected from the list comprising batch reactor, continuous stirred tank reactor, continuous fixed bed reactor and continuous fluidised bed reactor, preferably a batch reactor.

In the particular embodiment of the first aspect of the invention, the reactor is a batch reactor, the contact between the reagent and catalysts A and B is performed at a temperature ranging between 50° C. and 450° C., preferably between 130° C. and 350° C. In this method, the weight ratio between the reagent and the catalysts is preferably between 2 and 200, preferably between 5 and 100. Furthermore, it is performed during a time interval ranging between 2 minutes and 200 hours, preferably between 1 hour and 100 hours.

In another embodiment of the first aspect of the present invention, the contact between ethanol, n-hexanol and catalysts A and B is performed at a pressure of up to 120 bar, preferably between 20 and 80 bar.

In another embodiment of the first aspect of the present invention, the contact between ethanol, n-hexanol and catalysts A and B is performed under an atmosphere of nitrogen, argon, hydrogen or any mixture thereof, preferably in a nitrogen and hydrogen atmosphere. Normally, normally greater selectivities to 1-octanol are produced in the presence of hydrogen.

A second aspect of the present invention relates to the use of catalysts A and B, wherein catalyst A comprises:
i) a metal oxide comprising the following metals:
M1 is a divalent metal selected from Mg, Zn, Cu, Co, Mn, Fe, Ni, Ca and any mixture thereof,
M2 is Trivalent Ga; and
ii) a noble metal selected from Pd, Pt, Ru, Rh, Re and any mixture thereof;
and catalyst B comprises a metal oxide comprising the following metals:
M3 is a divalent metal selected from Mg, Zn, Cu Co, Mn, Fe, Ni, Ca and any mixture thereof,
M4 is a trivalent metal selected from Al, La, Fe, Cr, Mn, Co, Ni and any mixture thereof,
with the condition that catalyst B comprises at least Cu, Ni or any combination thereof; to produce 1-octanol.

In an embodiment of the second aspect of the present invention, the metal oxide of catalyst A further comprises an M5 metal, wherein M5 is at least one trivalent metal selected from Al, La, Fe, Cr, Mn, Co and Ni, preferably M5 comprises Al, more preferably M5 is Al.

In another embodiment of the second aspect of the present invention, catalyst A is produced by means of a method comprising the following steps:
a) total or partial thermal decomposition of a hydrotalcite $HT_A$ with the formula wherein:

M1, M2 and M5 have been previously defined, $Q_A$ is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II), x is a value between 0 and 0.5; y is a value between 0.00001 and 0.49; m is an integer between 1 and 4; and n is greater than 0, preferably n is a value between 1 and 100, and more preferably between 1 and 20.

b) addition to the metal oxide produced in step a) of:
a noble metal selected from Pd, Pt, Ru, Rh, Re and any mixture thereof.

With respect to the anion, $Q_A$ is preferably at least one anion selected from the list comprising $CO_3^{2-}$, $HCO_3^-$, $O_2^-$, $OH^-$, $Cl^-$, $NO_3^{2-}$, $Cl^-$, $F^-$, $Br^-$, $I^-$, $ClO_4^-$, $CH_3COO^-$, $C_6H_5COO$ and $SO_4^{2}$; even more preferably, $CO_3^{2-}$, $HCO_3^-$, $O_2^-$ and $OH^-$.

In another embodiment of the second aspect of the present invention, the hydrotalcite $HT_A$ is produced by the co-precipitation of M1, M2 and M5 compounds.

In another embodiment of the second aspect of the present invention, M1 is a divalent metal selected from Mg, Ca and any mixture thereof, preferably M1 is Mg.

Preferably, the co-precipitation is performed in aqueous phase. The co-precipitation of the compounds may be preferably performed after the addition of a solution of at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II) to a solution of at least one compound of M1, at least one compound of M2 and at least one compound of M5. This anion may be introduced between the layers of the resulting hydrotalcite. Sodium and/or potassium salts thereof may be used in order to produce solutions of the anion. Preferably, the at least one anion is selected from carbonate, bicarbonate and hydroxide. The best results are produced when the co-precipitation is performed at a pH higher than 7, preferably between 10 and 14. Furthermore, with the aim of regulating the pH, preferably sodium and/or potassium hydroxide are used.

Preferably, prior to the precipitation of said compounds, there is dissolution of at least one compound of M1, at least one compound of M2 and at least one compound of M5. Soluble M1, M2 and M5 compounds are understood to mean any salt which, when placed in contact with a solvent, dissociates, preferably in a polar solvent, more preferably water. Examples of soluble M1, M2 and M5 compounds may be nitrates, halides, sulfates, carboxylates and, in general, oxoacids comprising M1, M2 or M5; preferably, the soluble M1, M2 and M5 compounds are nitrates.

In another embodiment of the second aspect of the present invention, catalyst B is produced by means of a method comprising a step of total or partial thermal decomposition of a hydrotalcite $HT_B$ with the formula:

$$[M3_{(1-z)}M4_z(OH)_2][Q_B^{p-}{}_{(z/n)} \cdot rH_2O], \text{ wherein:}$$

M3 and M4 have been previously defined, $Q_B$ is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II), z is a value higher than 0 and lower than 1, preferably z is a value between 0.1 and 0.8; p is an integer between 1 and 4; and r is higher than 0, preferably r is a value between 1 and 100, and more preferably between 1 and 20.

With respect to the anion, $Q_B$ is preferably at least one anion selected from the list comprising $CO_3^{2-}$, $HCO_3^-$, $O_2^-$, $OH^-$, $Cl^-$, $NO_3^{2-}$, $Cl^-$, $F^-$, $Br^-$, $I^-$, $ClO_4^-$, $CH_3COO^-$, $C_6H_5COO^-$ and $SO_4^{2-}$; even more preferably, $CO_3^{2-}$, $HCO_3^-$, $O_2^-$ and $OH^-$.

In another embodiment of the second aspect of the present invention, the hydrotalcite $HT_B$ is produced by the co-precipitation of M3 and M4 compounds.

In another embodiment of the second aspect of the present invention, M3 is a divalent metal selected from Mg, Ca, Cu, Ni and any mixture thereof, preferably M3 is a divalent metal selected from Mg, Cu, Ni and any mixture thereof.

In another embodiment of the second aspect of the present invention, M4 is a trivalent metal selected from Al, Ni and any mixture thereof. More preferably M4 is Al.

In another embodiment of the second aspect of the present invention, catalyst B comprises Cu and Ni. The Ni may be both divalent and trivalent, preferably the Ni is divalent. Preferably catalyst B comprises Mg, Al, Cu and Ni.

In another embodiment of the second aspect of the present invention, if catalyst B only has Ni, the concentration of Ni is between 0.1% and 10% by weight with respect to the total of catalyst B. In another embodiment of the second aspect of the present invention, if the catalyst only has Cu, the concentration of Cu is between 0.1% and 10% by weight with respect to the total weight of catalyst B. In another embodiment of the second aspect of the present invention, the sum of the concentrations of Cu and Ni is between 0.2% and 10% by weight with respect to the total of catalyst B. These percentages refer to a weight of Cu and/or Ni not by weight of equivalent oxides.

In an embodiment of the second aspect of the present invention, the molar ratio (Mg+Cu+Ni/Al) is between 1 and 6, preferably between 2 and 5.

Preferably, the co-precipitation is performed in aqueous phase. The co-precipitation of the compounds may be preferably performed after the addition of a solution of at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II) to a solution of at least one compound of M3 and at least one compound of M4. This anion may be introduced between the layers of the resulting hydrotalcite. Sodium and/or potassium salts thereof may be used in order to produce solutions of the anion. Preferably, the at least one anion is selected from carbonate, bicarbonate and hydroxide. The best results are produced when the co-precipitation is performed at a pH higher than 7, preferably between 10 and 14. Furthermore, with the aim of regulating the pH, preferably sodium and/or potassium hydroxide are used.

Preferably, prior to the precipitation of said compounds, there is dissolution of at least one compound of M3 and at least one compound of M4. Soluble M3 and M4 compounds are understood to mean any salt which, when placed in contact with a solvent, dissociates, preferably in a polar solvent, more preferably water. Examples of soluble M3 and M4 compounds may be nitrates, halides, sulfates, carboxylates and, in general, oxoacids comprising M3 or M4; preferably, the soluble M3 and M4 compounds are nitrates.

In another embodiment of the second aspect of the present invention, the weight ratio of catalysts A and B is between 1:10 to 10:1, preferably is 1:5 to 5:1, and more preferably is 1:1.

In another embodiment of the second aspect of the present invention, the thermal decomposition of the hydrotalcites $HT_A$ and $HT_B$ is performed by means of calcination under atmosphere of oxygen, nitrogen or any mixture thereof at a temperature ranging between 250° C. and 650° C., preferably between 350° C. and 550° C. The thermal decomposition of the hydrotalcites is preferably performed during an interval of 0.5 to 48 hours, preferably between 1 and 24 hours. This method may be performed by heating the hydrotalcites in a gaseous atmosphere and may be performed in a static oven or a calcination reactor with a controlled gas flow, the latter being the preferred system. The gas may be an oxidising gas or a non-oxidising gas. Examples of oxidising gases may include air and oxygen. Examples of non-oxidising gases may be inert gases, such as nitrogen, argon, helium and reducing gases, such as, for example, carbon dioxide, hydrogen and ammonia. Preferably, the calcination is performed in the presence of oxygen, nitrogen or mixtures thereof, and, even more preferably, in the presence of oxygen and nitrogen.

In another embodiment of the second aspect of the present invention, the noble metal of catalyst A is added to the metal oxide by wet impregnation, incipient volume impregnation or deposition-precipitation, preferably the noble metal is added to the metal oxide by wet impregnation, incipient volume impregnation or deposition-precipitation, more preferably by incipient volume impregnation. The incipient volume impregnation method, also called incipient wetness impregnation method, is based on the use of a minimum quantity of liquid for the impregnation, only that which is necessary to reach the maximum saturation of the corresponding solid.

In another embodiment of the second aspect of the present invention, the noble metal of catalyst A comprises Pd, preferably the noble metal is Pd. The best yields for 1-octanol have been produced when the calcinated hydrotalcites containing Ga are impregnated with Pd.

In another embodiment of the second aspect of the present invention, the concentration of the noble metal in catalyst A ranges from 0.001% and 10% by weight with respect to catalyst A total, preferably between 0.01% and 5%.

In another embodiment of the second aspect of the present invention, there is a calcination step after the addition of the noble metal of catalyst A. This calcination is preferably calcination in an atmosphere of oxygen, nitrogen or any mixture thereof. This calcination is preferably performed at a temperature ranging between 250° C. and 650° C., and, even more preferably, between 350° C. and 550° C. This calcination is preferably performed during an interval ranging between 0.5 and 48 hours, preferably between 1 and 24 hours, and, even more preferably, between 1 and 6 hours. This method may be performed by heating the material derived from hydrotalcite $HT_A$ in a gaseous atmosphere and may be performed in a static oven or a calcination reactor with a controlled gas flow, the latter being the preferred system. The gas may be an oxidising gas or a non-oxidising gas. Examples of oxidising gases may include air and oxygen. Examples of non-oxidising gases may be inert gases, such as nitrogen, argon, helium and reducing gases, such as, for example, carbon dioxide, hydrogen and ammonia. Preferably, the calcination is performed in the presence of oxygen, nitrogen or mixtures thereof, and, even more preferably, in the presence of oxygen and nitrogen.

In a preferred embodiment of the second aspect of the present invention, the method of the invention as previously described further comprises a reduction step after the calcination subsequent to the addition of the noble metal of catalyst A. During the reduction, the noble metal, which acts as one of the main active sites in the method, is reduced. This reduction step is preferably performed in an $H_2$ atmosphere and, preferably, at a temperature ranging between 200° C. and 500° C., more preferably between 250° C. and 450° C. This reduction is preferably performed during an interval between 0.5 and 48 hours, preferably between 1 and 24 hours, and, even more preferably, between 1 and 6 hours. Preferably, the reduction take place immediately prior to the contact step with the reagent, i.e. with ethanol and hexanol.

In another embodiment of the second aspect of the present invention, there is a calcination step after the addition of the noble metal of catalyst A and a reduction step subsequent to said calcination.

In another preferred embodiment of the second aspect of the invention, the contact between ethanol, n-hexanol and catalysts A and B is performed in a reactor selected from the list comprising batch reactor, continuous stirred tank reactor, continuous fixed bed reactor and continuous fluidised bed reactor, preferably a batch reactor.

In the particular embodiment of the second aspect of the invention, the reactor is a batch reactor, the contact between the reagent and catalysts A and B is performed at a temperature ranging between 50° C. and 450° C., preferably between 130° C. and 350° C. In this method, the weight ratio between the reagent and the catalysts is preferably between 2 and 200, preferably between 5 and 100. Furthermore, it is performed during a time interval ranging between 2 minutes and 200 hours, preferably between 1 hour and 100 hours.

In another embodiment of the second aspect of the present invention, the contact between ethanol, n-hexanol and catalysts A and B is performed at a pressure of up to 120 bar, preferably between 20 and 80 bar.

In another embodiment of the second aspect of the present invention, the contact between ethanol, n-hexanol and catalysts A and B is performed under atmosphere of nitrogen, argon, hydrogen or any mixture thereof, preferably in a nitrogen and hydrogen atmosphere. Normally, greater selectivities to 1-octanol are produced in the presence of hydrogen.

Unless defined otherwise, all the technical and scientific terms used in the present document have the same meaning as is commonly understood by a person skilled in the art the present invention belongs to. Similar or equivalent methods or materials to those described can be used in the practice of the present invention. Throughout the description and the claims, the word "comprises" and the variants thereof are not intended to exclude other technical characteristics, additives, components or steps.

For persons skilled in the art, other objects, advantages and characteristics of the invention will arise partly from the description and partly from the practise of the invention. The following examples and figures are provided for illustrative purposes, and are not intended to limit the scope of the present invention

EXAMPLES

Below, the present inventors shall illustrate, by means of assays performed by the inventors, that demonstrate the efficacy of the hydrotalcite-derived catalysts comprising gallium in their structure used together with hydrotalcite-derived catalysts comprising Cu, Ni or any mixture thereof in the production of 1-octanol.

Example 1. Synthesis of the 0.16% Ga-HT-1 Catalyst

It was prepared by means of a standard co-precipitation method using two solutions. The first solution contained 18.50 g of $Mg(NO_3)_2.6H_2O$, 26.75 g of $Al(NO_3)_3.9H_2O$ and 0.06 g of $Ga(NO_3)_3.9H_2O$, dissolved in 50.61 g of Milli-Q water, with a molar concentration of (Al+Mg+Ga) of 1.5. The second solution contained 14.40 g of NaOH and 10.40 g of $Na_2CO_3$ in 70.83 g of Milli-Q water, and it was used to produce the suitable precipitation of the Mg, Al and Ga species, and to set the pH of the total mixture at $\approx$13. Both solutions were added, at a total flow rate of 30 ml/h for approximately 4 h, to a receptacle under vigorous stirring at ambient temperature. The gel formed was aged at ambient temperature for 1-2 h; it was then filtered and washed with distilled water until the carbonate was not detected in the filtered liquid (at pH$\approx$7). Next, the solid was dried in an oven at 60° C. for 14-16 h. The hydrotalcite (Ga-HT-1) produced was calcined in air at 450° C. for 3-4 h, to produce a mixed oxide with a molar ratio of Mg/Al$\approx$1.48, a Ga content of 0.16% by weight (measured by chemical analysis and ICP-MS) and a surface area (BET method) of 319 $m^2$/g.

Example 2. Synthesis of the 0.29% Ga-HT-4 Catalyst

It was prepared by means of a standard co-precipitation method using two solutions. The first solution contained 29.89 g of $Mg(NO_3)_2.6H_2O$, 10.90 g of $Al(NO_3)_3.9H_2O$ and 0.06 g of $Ga(NO_3)_3.9H_2O$, dissolved in 55.18 g of Milli-Q water, with a molar concentration of (Al+Mg+Ga) of 1.5. The second solution contained 12.52 g of NaOH and 10.52 g of $Na_2CO_3$ in 72.60 g of Milli-Q water, and it was used to produce the suitable precipitation of the Mg, Al and Ga species, and to set the pH of the total mixture at $\approx$13. Both solutions were added, at a total flow rate of 30 ml/h for approximately 4 h, to a receptacle under vigorous stirring at ambient temperature. The gel formed was aged at ambient temperature for 1-2 h; it was then filtered and washed with distilled water until the carbonate was not detected in the filtered liquid (at pH$\approx$7). Next, the solid was dried in an oven at 60° C. for 14-16 h. The hydrotalcite (Ga-HT-4) produced was calcined in air at 450° C. for 3-4 h, to produce a mixed oxide with a molar ratio of Mg/Al$\approx$3.8, a Ga content of 0.29% by weight (measured by chemical analysis and ICP-MS) and a surface area (BET method) of 262 $m^2$/g.

Example 3. Synthesis of the 0.63% Pd/0.16% Ga-HT-1 Catalyst

It was prepared from the material prepared as described in Example 1, wherein the incorporation of Pd (1.0% by weight, theoretical) in the Ga-HT-1 material was performed by means of the incipient wetness impregnation method, using, in this case, 0.025 g of $Pd(NH_3)_4Cl_2.6H_2O$ dissolved in 2.000 g of Milli-Q water, to impregnate 1.003 g of 0.16% of Ga-HT-1. Once impregnated, the solid produced was dried in an oven at 100° C. for 14-16 h; it was then calcined in air at 450° C. for 3-4 h, and, was subsequently reduced to 350° C. in an $H_2$ atmosphere for 3 h prior to the catalytic application thereof. The resulting Pd/0.16% Ga-HT-1 material, characterised by chemical analysis and ICP-MS, contained$\approx$0.63% by weight of Pd.

Example 4. Synthesis of the 0.24% Pd/0.29% Ga-HT-4 Catalyst

It was prepared from the material prepared as described in Example 2, wherein the incorporation of Pd (0.3% by weight, theoretical) into the Ga-HT-4 material was performed by means of the incipient wetness impregnation method, using, in this case, 0.008 g of $Pd(NH_3)_4Cl_2.6H_2O$ dissolved in 1.800 g of Milli-Q water, to impregnate 1.011 g of 0.29% of Ga-HT-4. Once impregnated, the solid produced was dried in an oven at 100° C. for 14-16 h; it was then calcined in air at 450° C. for 3-4 h, and, was subsequently reduced to 350° C. in an $H_2$ atmosphere for 3 h prior to the catalytic application thereof. The resulting Pd/0.29% Ga-HT-4 material, characterised by chemical analysis and ICP-MS, contained$\approx$0.24% by weight of Pd.

Example 5. Synthesis of the 2.5% Cu-HT-4 Catalyst

It was prepared by means of a standard co-precipitation method using two solutions. The first solution contained 30.01 g of $Mg(NO_3)_2.6H_2O$, 10.16 g of $Al(NO_3)_3.9H_2O$ and 0.58 g of $Cu(NO_3)_2.2.5H_2O$, dissolved in 57.01 g of Milli-Q water, with a molar concentration of (Al+Mg+Cu) of 1.5. The second solution contained 12.80 g of NaOH and 10.37 g of $Na_2CO_3$ in 74.58 g of Milli-Q water, and it was used to produce the suitable precipitation of the Mg, Al and Cu species, and to set the pH of the total mixture at $\approx$13. Both solutions were added (total flow rate=30 ml/h for approximately 4 h) to a receptacle under vigorous stirring at ambient temperature. The gel formed was aged at ambient temperature for 1-2 h; it was then filtered and washed with distilled water until the carbonate was not detected in the filtered liquid (at pH$\approx$7). Next, the solid was dried in an oven at 60° C. for 18 h. The hydrotalcite (Cu-HT-4) produced was calcined in air at 450° C. for 3-4 h, to produce a mixed oxide with a molar ratio of Mg/Al$\approx$3.88, a Cu content of 2.5% by weight, characterised by chemical analysis and ICP-MS and a surface area (BET method) of 191 $m^2$/g.

Example 6. Synthesis of the 2.5% Ni-HT-4 Catalyst

It was prepared by means of a standard co-precipitation method using two solutions. The first solution contained 29.29 g of $Mg(NO_3)_2.6H_2O$, 10.94 g of $Al(NO_3)_3.9H_2O$ and 0.78 g of $Ni(NO_3)_2.6H_2O$, dissolved in 56.29 g of Milli-Q water, with a molar concentration of (Al+Mg+Cu) of 1.5. The second solution contained 12.88 g of NaOH and 10.38 g of $Na_2CO_3$ in 74.12 g of Milli-Q water, and it was used to produce the suitable precipitation of the Mg, Al and Cu species, and to set the pH of the total mixture at $\approx$13. Both solutions were added (total flow rate=30 ml/h for approximately 4 h) to a receptacle under vigorous stirring at ambient temperature. The gel formed was aged at ambient temperature for 1-2 h; it was then filtered and washed with distilled water until the carbonate was not detected in the filtered liquid (at pH≈7). Next, the solid was dried in an oven at 60° C. for 18 h. The hydrotalcite (Ni-HT-4) produced was calcined in air at 450° C. for 3-4 h, to produce a mixed oxide with a molar ratio of Mg/Al≈3.58, a Ni content of 2.5% by weight, characterised by chemical analysis and ICP-MS and a surface area (BET method) of 190 m$^2$/g.

Example 7. Synthesis of the 0.77% Cu-0.92% Ni-HT-4 Catalyst

It was prepared by means of a standard co-precipitation method using two solutions. The first solution contained 29.25 g of Mg(NO$_3$)$_2$.6H$_2$O, 10.86 g of Al(NO$_3$)$_3$.9H$_2$O, 0.28 g of Cu(NO$_3$)$_2$.2.5H$_2$O and 0.39 g of Ni(NO$_3$)$_2$.6H$_2$O, dissolved in 55.69 g of Milli-Q water, with a molar concentration of (Al+Mg+Cu) of 1.5. The second solution contained 12.82 g of NaOH and 10.31 g of Na$_2$CO$_3$ in 72.70 g of Milli-Q water, and it was used to produce the suitable precipitation of the Mg, Al and Cu species, and to set the pH of the total mixture at ≈13. Both solutions were added (total flow rate=30 ml/h for approximately 4 h) to a receptacle under vigorous stirring at ambient temperature.

The gel formed was aged at ambient temperature for 1-2 h; it was then filtered and washed with distilled water until the carbonate was not detected in the filtered liquid (at pH≈7). Next, the solid was dried in an oven at 60° C. for 18 h. The hydrotalcite (Cu—Ni-HT-4) produced was calcined in air at 450° C. for 3-4 h, to produce a mixed oxide with a molar ratio of Mg/Al≈3.99, Cu and Ni contents of 0.77 and 0.92% by weight, respectively, characterised by chemical analysis and ICP-MS and a surface area (BET method) of 208 m$^2$/g.

Example 8. Comparative Catalytic Activity of the Catalysts of Examples 3 to 7 Under N$_2$ Atmosphere 1750 mg of ethanol, 1790 mg of n-hexanol and 350 mg of one of the catalytic materials of Examples 3 to 7 (or physical mixtures thereof) were introduced in a 12 ml stainless steel autoclave reactor, with a reinforced PEEK (polyether ethyl ketone)-coated inside and a magnetic stirrer. The reactor was hermetically closed, with the system having a connector to a pressure meter (manometer), another connector for the loading of gases and a third outlet which made it possible to take samples at different time intervals. The reactor was initially pressurised with 24 bar of N$_2$ and was heated to 250° C. under continuous stirring, until the total system pressure reached approx. 35-40 bar (reaction time=0). Liquid samples were taken (≈50-100 µl) in different time intervals until 17 hours of reaction. The samples were filtered and diluted in a 2% by weight of chlorobenzene in acetonitrile standard solution, and they were analysed by means of gas chromatography in a GC-3900 Varian equipped with an FID detector and a 60 m TRB-624 capillary column.

The ethanol conversion, in molar percentage (EtOH conv.), was calculated from the composition of the mixture obtained:

(initial moles of ethanol–final moles of ethanol)/
(initial moles of ethanol*100)

The n-hexanol conversion, in molar percentage (Cony. of n-HexOH), was calculated from the composition of the mixture obtained:

(initial moles of *n*-hexanol–final moles of *n*-hexanol)/(initial moles of *n*-hexanol*100)

The total yield of n-butanol, in molar percentage (Yield of n-ButOH), was calculated as:

(moles of *n*-butanol/moles of total products)*EtOH conv./100

The total yield of 1-octanol, in molar percentage (Yield of 1-OctOH) was calculated as:

(moles of 1-octanol/moles of total products)*EtOH conv./100

The total yield of linear C$_{4+}$ alcohols, in molar percentage (Yield of linear C$_{4+}$OH), including n-butanol and 1-octanol, of course, was calculated as:

(moles of linear C$_{4+}$/moles of total products)*EtOH conv./100

The total yield of branched C$_{4+}$ alcohols, in molar percentage (Yield of branched C$_{4+}$OH), was calculated as:

(moles of branched C$_{4+}$/moles of total products)* EtOH conv./100

In this way, the following results were obtained:

TABLE 1

Catalytic activity of the different mixed metal oxides and of physical mixtures thereof in the transformation of ethanol + n-hexanol under nitrogen atmosphere.

| Ex. | Catalyst | T (h) | EtOH conv. | n-HexOH conv. | n-ButOH yield | 1-OctOH yield | C$_{4+}$OH yield Lin. | C$_{4+}$OH yield Bra. |
|---|---|---|---|---|---|---|---|---|
| 3 | 0.63% Pd/0.16% Ga-HT-1 | 5 | 52.3 | 15.6 | 22.1 | 7.60 | 30.3 | 2.6 |
| 4 | 0.24% Pd/0.29% Ga-HT-4 | 5 | 41.1 | 20.2 | 22.0 | 6.90 | 30.0 | 2.6 |
| 5 | 2.5% Cu/HT-4 | 5 | 49.8 | 19.2 | 22.5 | 6.64 | 29.1 | 0.9 |
| 6 | 2.5% Ni-HT-4 | 5 | 42.1 | 16.3 | 9.1 | 4.30 | 13.7 | 0.4 |
| 7 | 0.77% Cu-0.92% Ni-HT-4 | 5 | 51.4 | 16.2 | 26.8 | 8.00 | 36.8 | 2.9 |
| 3 + 7 | 0.63% Pd/0.16% Ga-HT-1 (0.25 g) + 0.77% Cu-0.92% Ni-HT-4 (0.10 g) | 5 | 49.2 | 17.3 | 26.3 | 10.82 | 39.0 | 3.6 |
| 4 + 5 | 0.24% Pd/0.29% Ga-HT-4 (0.20 g) + 2.5% Cu-HT-4 (0.15 g) | 5 | 29.5 | 9.4 | 15.0 | 7.71 | 24.0 | 1.9 |
| 4 + 6 | 0.24% Pd/0.29% Ga-HT-4 (0.20 g) + 2.5% Ni-HT-4 (0.15 g) | 5 | 28.4 | 13.4 | 18.0 | 5.33 | 23.3 | 0.7 |
| 4 + 7 | 0.24% Pd/0.29% Ga-HT-4 (0.20 g) + 0.77% Cu-0.92% Ni-HT-4 (0.15 g) | 5 | 39.7 | 10.1 | 23.0 | 8.56 | 31.6 | 2.1 |

Figure 1:
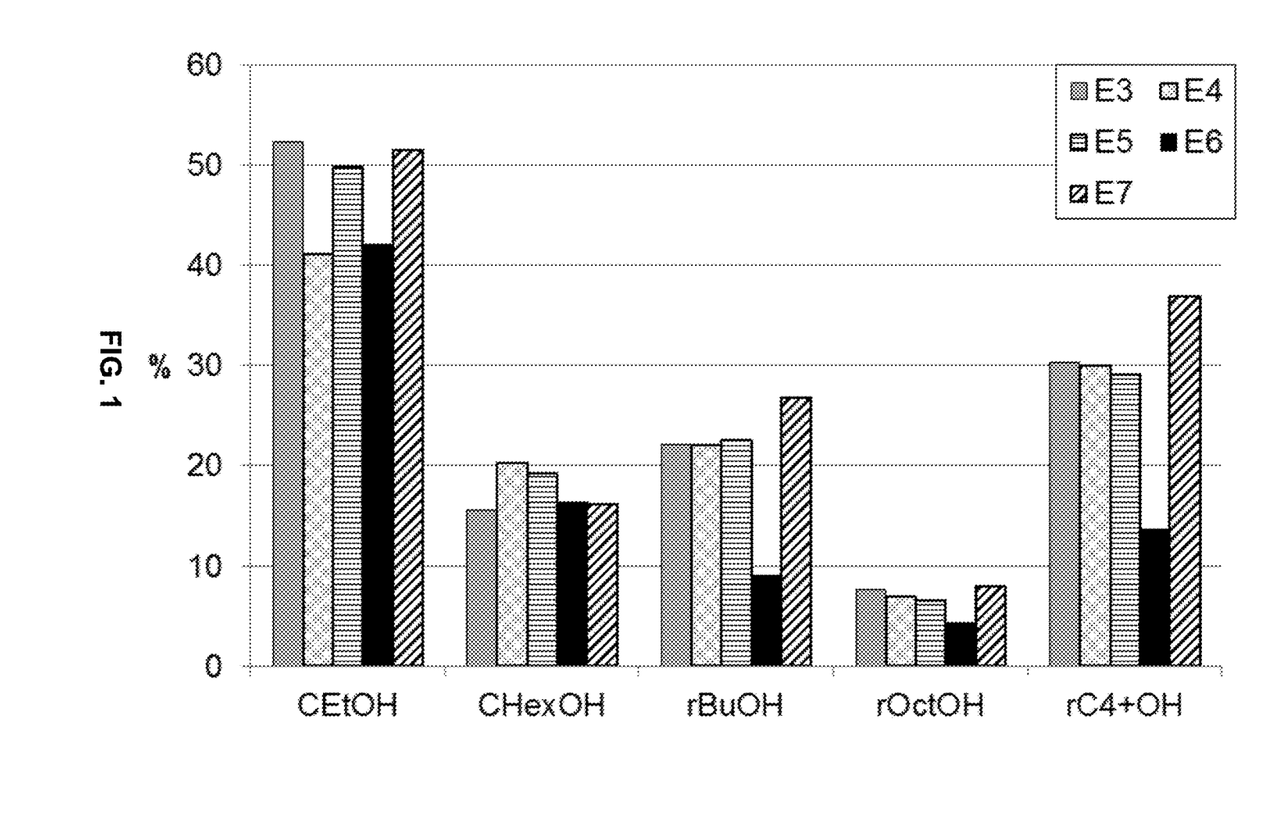
FIG. 1. Shows a comparative graph of the catalytic activities (conversions of EtOH and HexOH and yields of n-ButOH, 1-OctOH and of the sum of $C_{4+}OH$) of catalysts based on different mixed oxides derived from hydrotalcites (Examples 3 to 7) in a $N_2$ atmosphere. %: percentage of conversion or yield, as indicated on the x-axis; CEtOH: ethanol conversion, CHexOH: n-hexanol conversion, rButOH: yield of n-ButOH; rOctOH: yield of 1-octanol; rC4+OH: yield of alcohols C4+; E3, example 3 (0.63% Pd/0.16% Ga-HT-1); E4, example 4 (0.24% Pd/0.29% Ga-HT-4); E5, example 5 (2.5% Cu/HT-4); E6, example 6 (2.5% Ni-HT-4); E7, example 7 (0.77% Cu-0.92% Ni-HT-4).
Figure 2:
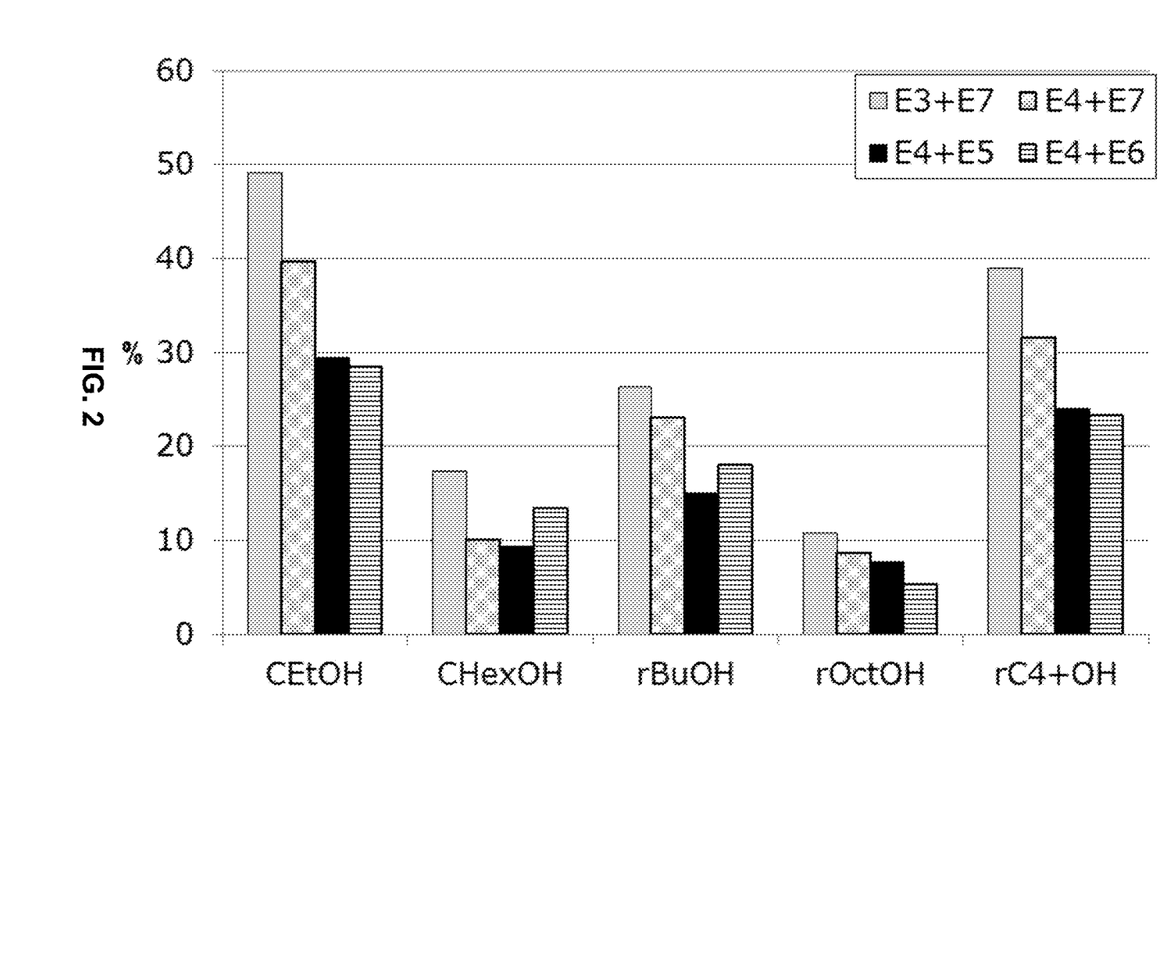
FIG. 2. Shows a comparative graph of the catalytic activities (conversions of EtOH and HexOH and yields of n-ButOH, 1-OctOH and of the sum of C4+OH) of physical mixtures of catalysts based on different mixed oxides derived from hydrotalcites (Examples 3+7, 4+7, 4+5 and 4+6) in a $N_2$ atmosphere. %: percentage of conversion or yield, as indicated on the x-axis; CEtOH: ethanol conversion, CHexOH: n-hexanol conversion, rButOH: yield of n-ButOH; rOctOH: yield of 1-octanol; rC4+OH: yield of alcohols C4+; E3, example 3 (0.63% Pd/0.16% Ga-HT-1); E4, example 4 (0.24% Pd/0.29% Ga-HT-4); E5, example 5 (2.5% Cu/HT-4); E6, example 6 (2.5% Ni-HT-4); E7, example 7 (0.77% Cu-0.92% Ni-HT-4).

The comparison of the results of the physical mixtures of the catalysts of Examples 3+7, 4+5, 4+6, and 4+7 show that the best results are produced with the mixtures of Examples 3+7 and 4+7. Even more so, these mixtures of catalysts show better results to those produced with the individual catalysts, which implies there is a synergic factor and not only additive with the use of the physical mixtures of the catalysts. In particular, the combination of the catalyst comprising Ga (Example 3) with the catalyst of Example 7 (Cu—Ni-HT-4) is particularly noteworthy, which gives higher yields of 1-octanol and, in general, higher yield of $C_{4+}$ alcohols than the respective catalysts used individually, as observed in FIGS. 1 and 2.

Example 9. Comparative Catalytic Activity of the Catalysts of Examples 3 and 7 and of Physical Mixtures Thereof Under $N_2$ Atmosphere 1750 mg of ethanol, 1790 mg of n-hexanol and 350 mg of one of the catalytic materials of Examples 3 and 7 and of physical mixtures of different proportions thereof (always giving a total of 350 mg) were introduced in a 12 ml stainless steel autoclave reactor, with a reinforced PEEK (polyether ethyl ketone)-coated inside and a magnetic stirrer. The reactor was hermetically closed, with the system having a connector to a pressure meter (manometer), another connector for the loading of gases and a third outlet which made it possible to take samples at different time intervals. The reactor was initially pressurised with 20 bar of $N_2$ and was heated to 250° C. under continuous stirring, until the total system pressure reached approx. 35-40 bar (reaction time=0). Liquid samples were taken (≈50-100 μl) in different time intervals until 17 hours of reaction. The samples were filtered and diluted in a 2% by weight of chlorobenzene in acetonitrile standard solution, and they were analysed by means of gas chromatography in a GC-3900 Varian equipped with an FID detector and a 60 m TRB-624 capillary column.

The ethanol conversion, in molar percentage (EtOH conv.), was calculated from the composition of the mixture obtained:

(initial moles of ethanol−final moles of ethanol)/ (initial moles of ethanol*100)

The n-hexanol conversion, in molar percentage (Cony of n-HexOH), was calculated from the composition of the mixture obtained:

(initial moles of $n$-hexanol−final moles of $n$-hexanol)/(initial moles of $n$-hexanol*100)

The total yield of n-butanol, in molar percentage (Yield of n-ButOH), was calculated as:

(moles of $n$-butanol/moles of total products)*EtOH conv./100

The total yield of 1-octanol, in molar percentage (Yield of 1-OctOH) was calculated as:

(moles of 1-octanol/moles of total products)*EtOH conv./100

The total yield of linear $C_{4+}$ alcohols, in molar percentage (Yield of linear $C_{4+}OH$), including n-butanol and 1-octanol, of course, was calculated as:

(moles of linear $C_{4+}$/moles of total products)*EtOH conv./100

The total yield of branched $C_{4+}$ alcohols, in molar percentage (Yield of branched $C_{4+}OH$), was calculated as:

(moles of branched $C_{4+}$/moles of total products)* EtOH conv./100

In this way, the following results were obtained:

TABLE 2

Catalytic activity of the catalysts 0.63% Pd/0.16% Ga-HT-1 and 0.77% Cu—0.92% Ni-HT-4 and of physical mixtures of different proportions thereof in the transformation of ethanol + n-hexanol under nitrogen atmosphere.

| Ex. | Catalyst | T (h) | EtOH conv. | n-HexOH conv. | n-ButOH yield | 1-OctOH yield | $C_{4+}$OH yield Lin. | Bra. |
|---|---|---|---|---|---|---|---|---|
| 3 | 0.63% Pd/0.16% Ga-HT-1 | 5 | 52.3 | 15.6 | 22.1 | 7.60 | 30.3 | 2.6 |
| 3 + 7 | 0.63% Pd/0.16% Ga-HT-1 (0.25 g) + 0.77% Cu-0.92% Ni-HT-4 (0.10 g) | 5 | 49.2 | 17.3 | 26.3 | 10.82 | 39.0 | 3.6 |
| 3 + 7 | 0.63% Pd/0.16% Ga-HT-1 (0.20 g) + 0.77% Cu-0.92% Ni-HT-4 (0.15 g) | 5 | 58.0 | 19.9 | 26.0 | 13.5 | 42.3 | 3.5 |
| 3 + 7 | 0.63% Pd/0.16% Ga-HT-1 (0.10 g) + 0.77% Cu-0.92% Ni-HT-4 (0.25 g) | 5 | 51.7 | 14.6 | 25.2 | 11.17 | 38.5 | 3.5 |
| 7 | 0.77% Cu-0.92% Ni-HT-4 | 5 | 51.4 | 16.2 | 26.8 | 8.00 | 36.8 | 2.9 |

Figure 3:
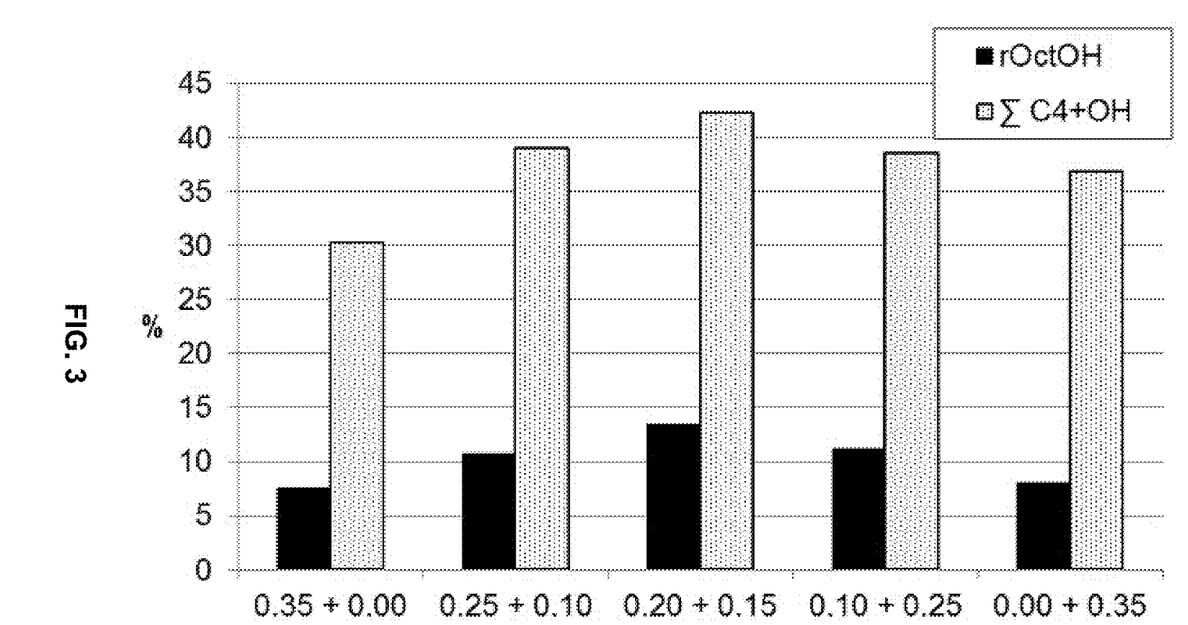
FIG. 3. Shows a comparative graph of the catalytic activities (yields of 1-OctOH and of the sum of $C_{4+}OH$) of physical mixtures in different proportions or ratios of the catalysts of Examples 3 and 7 in a $N_2$ atmosphere %: percentage of yield; r(OctOH): yield of 1-octanol; r($\Sigma$C4+OH): yield of the sum of C4+OH (in points); g cat; quantity in grams of catalyst of the Example 3 (0.63% Pd/0.16% Ga-HT-1)+quantity in grams of catalyst of the Example 7 (0.77% Cu-0.92% Ni-HT-4).

If the physical mixtures were compared in different proportions of the catalysts of Examples 3 and 7, the results show that a synergic effect is observed and not merely additive with the use of the catalyst mixture, and that furthermore, there is an optimum in the proportions of each one of the catalysts. Thus, the greatest yields of 1-octanol and, in general, greater yield of $C_{4+}$ alcohols were observed with the ratio in the mixture of 200 mg of the catalyst of Example 3 (Pd/Ga-HT-1) and 150 mg of the catalyst of Example 7 (Cu—Ni-HT-4), as observed in FIG. 3. This demonstrates that not only the synergic effect of the catalyst mixture with respect to the individual catalysts, but also both the type of catalyst and its proportions are not trivial, nor can they be calculated or pre-established beforehand taking the data obtained with each individual catalyst as the base.

Example 10. Comparative Catalytic Activity of the Catalysts of Examples 3, 5-7 and the Physical Mixture of the Catalysts of Examples 3 and 7 Under $H_2$ (or $N_2$) Atmosphere with Ethanol Alone (without n-Hexanol)

3500 mg of ethanol and 350 mg of one of the catalytic materials of Examples 3 and 5 to 7, as well as the mixture of Examples 3 (200 mg) and 7 (150 mg) were introduced in a 12 ml stainless steel autoclave reactor, with a reinforced PEEK (polyether ethyl ketone)-coated inside and a magnetic stirrer. The reactor was hermetically closed, with the system having a connector to a pressure meter (manometer), another connector for the loading of gases and a third outlet which made it possible to take samples at different time intervals The reactor was initially pressurised with 10 bar of $H_2$ and next it was taken to 24 bar with addition of $N_2$ and was heated to 200° C. under continuous stirring, until the total system pressure reached approx. 30 bar (reaction time=0). Liquid samples were taken (≈50-100 μl) in different time intervals until 17 hours of reaction. The samples were filtered and diluted in a 2% by weight of chlorobenzene in acetonitrile standard solution, and they were analysed by means of gas chromatography in a GC-3900 Varian equipped with an FID detector and a 60 m TRB-624 capillary column.

The following results were obtained:

TABLE 3

Catalytic activity of the catalysts of Examples 3, 5-7 and the mixture of the catalysts of Examples 3 and 7 in the transformation of ethanol under hydrogen (or nitrogen) atmosphere.

| Ex. | Catalyst | T (h) | EtOH conv. | n-HexOH conv. | n-HexOH yield | 1-OctOH yield | $C_{4+}$OH yield Lin. | Bra. |
|---|---|---|---|---|---|---|---|---|
| 3 | 0.63% Pd/0.16% Ga-HT-1 | 5 | 11.2 | 8.8 | 0.0 | 0.0 | 8.8 | 0.0 |
| 5 | 2.5% Cu/HT-4 | 5 | 7.7 | 5.7 | 0.8 | 0.0 | 6.5 | 0.0 |
| 5 | 2.5% Cu/HT-4 (Sin $H_2$) | 5 | 9.4 | 4.7 | 1.5 | 0.0 | 6.2 | 0.0 |
| 6 | 2.5% Ni-HT-4 | 5 | 6.9 | 4.8 | 0.7 | 0.0 | 5.5 | 0.0 |
| 6 | 2.5% Ni-HT-4 (Sin $H_2$) | 5 | 7.8 | 2.5 | 1.0 | 0.0 | 3.5 | 0.0 |
| 7 | 0.77% Cu-0.92% Ni-HT-4 | 5 | 10.7 | 8.4 | 0.2 | 0.0 | 8.6 | 0.0 |
| 3 + 7 | 0.63% Pd/0.16% Ga-HT-1 (0.25 g) + 0.77% Cu-0.92% Ni-HT-4 (0.10 g) | 5 | 13.2 | 4.9 | 7.5 | 0.33 | 12.7 | 0.1 |

The rest of the products up 100% mainly comprise aldehydes (ethanal, butanal, hexanal, ethylacetate and dietoxyethane).

The results obtained with the physical mixture of the catalysts of Examples 3 and 7 clearly show that it is possible to produce high yields of 1-hexanol (and the sum of 1-butanol+1-hexanol) using only ethanol as starting reagent. However, these results also show that both the individual catalysts and the physical mixture thereof object of the present invention do not produce 1-octanol in a high percentage when they react with ethanol as reagent. Therefore, it shows that n-hexanol and ethanol are required to produce high yields of 1-octanol.

Example 11. Comparative Catalytic Activity of the Catalysts of Examples 3, 5, 7 and of the Physical Mixture of the Catalysts of Examples 3 and 7 Under $H_2$ Atmosphere with n-Butanol as Raw Material (Neither Ethanol Nor n-Hexanol)

3500 mg of n-butanol and 350 mg of one of the catalytic materials of Examples 3, 5 and 7, and the mixture of Examples 3 (200 mg) and 7 (150 mg), were introduced in a 12 ml stainless steel autoclave reactor, with a reinforced PEEK (polyether ethyl ketone)-coated inside and a magnetic stirrer. The reactor was hermetically closed, with the system having a connector to a pressure meter (manometer), another connector for the loading of gases and a third outlet which made it possible to take samples at different time intervals The reactor was initially pressurised with 10 bar of $H_2$ and next it was taken to 24 bar with addition of $N_2$ and was heated to 250° C. under continuous stirring, until the total system pressure reached approx. 40 bar (reaction time=0). Liquid samples were taken (≈50-100 μl) in different time intervals until 17 hours of reaction. The samples were filtered and diluted in a 2% by weight of chlorobenzene in acetonitrile standard solution, and they were analysed by means of gas chromatography in a GC-3900 Varian equipped with an FID detector and a 60 m TRB-624 capillary column.

The following results were obtained:

TABLE 4

Catalytic activity of the catalysts of Examples 3, 7 and of physical mixtures of Examples 3 and 7 in the transformation of n-butanol under hydrogen atmosphere.

| Ex. | Catalyst | T (h) | n-ButOH conv. | Butanal yield | Aldehydes yield | 1-OctOH yield | $C_{4+}$OH yield Lin. | Bra. |
|---|---|---|---|---|---|---|---|---|
| 3 | 0.63% Pd/0.16% Ga-HT-1 | 5 | 22.2 | 2.5 | 1.2 | 1.1 | 11.9 | 3.3 |
| 7 | 0.77% Cu-0.92% Ni-HT-4 | 5 | 23.1 | 4.1 | 2.1 | 0.5 | 10.2 | 3.5 |
| 3 + 7 | 0.63% Pd/0.16% Ga-HT-1 (0.25 g) + 0.77% Cu-0.92% Ni-HT-4 (0.10 g) | 5 | 27.9 | 2.8 | 1.8 | 1.9 | 13.2 | 5.4 |

The rest of the products up to 100% mainly comprise 3-methyl-2-butanone, butyl butanoate, n-butyl ether, 4-methyl-2-hexanone, 1,1-dibutoxybutane.

These results show that both the individual catalysts and the physical mixture of catalysts object of the present invention do not produce 1-octanol in a high percentage. Therefore, it shows that n-hexanol and ethanol are required to produce high yields of 1-octanol.

The invention claimed is:

1. A method for producing 1-octanol comprising a contact step between ethanol, n-hexanol and two catalysts A and B, wherein catalyst A comprises:
   i) a metal oxide comprising the following metals:
   M1 is a divalent metal selected from Mg, Zn, Cu, Co, Mn, Fe, Ni, Ca and any mixture thereof,
   M2 is trivalent Ga; and
   ii) a noble metal selected from Pd, Pt, Ru, Rh, Re and any mixture thereof;
and catalyst B comprises a metal oxide comprising the following metals:
   M3 is a divalent metal selected from Mg, Zn, Cu Co, Mn, Fe, Ni, Ca and any mixture thereof,
   M4 is a trivalent metal selected from Al, La, Fe, Cr, Mn, Co, Ni and any mixture thereof,
with the condition that catalyst B comprises at least Cu, Ni or any combination thereof, wherein the Ni comprises divalent or trivalent Ni or any mixture thereof.

2. The method according to claim 1, wherein the metal oxide of catalyst A further comprises an M5 metal, wherein M5 is at least one trivalent metal selected from Al, La, Fe, Cr, Mn, Co and Ni.

3. The method according to claim 2, wherein catalyst A is produced by means of a method comprising the following steps:
   a) total or partial thermal decomposition of a hydrotalcite $HT_A$ with the formula wherein:

$Q_A$ is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II),
   x is a value between 0 and 0.5; y is a value between 0.00001 and 0.49; m is an integer between 1 and 4; and n is greater than 0,
   b) addition to the metal oxide produced in step a) of:
   a noble metal selected from Pd, Pt, Ru, Rh, Re and any mixture thereof.

4. The method according to claim 3, wherein the hydrotalcite $HT_A$ is produced by the co-precipitation of M1, M2 and M5 compounds.

5. The method according to claim 1, wherein M1 is a divalent metal selected from Mg, Ca and any mixture thereof.

6. The method according to claim 5, wherein M1 is Mg.

7. The method according to claim 2, wherein M5 comprises Al.

8. The method according to claim 1, wherein catalyst B is produced by means of a method comprising a step of total or partial thermal decomposition of a hydrotalcite $HT_B$ with the formula:

, wherein:

M3 is a divalent metal from Mg, Zn, Cu Co, Mn, Fe, Ni, Ca and any mixture thereof, and M4 is a trivalent metal selected from Al, La, Fe, Cr, Mn, Co, Ni and any mixture thereof, $Q_B$ is at least one anion selected from hydroxide, chloride, fluoride, bromide, iodide, nitrate, perchlorate, chlorate, bicarbonate, acetate, benzoate, methanesulfonate, p-toluenesulfonate, phenoxide, alkoxide, carbonate, sulfate, terephthalate, phosphate, hexacyanoferrate (III) and hexacyanoferrate (II), z is a value higher than 0 and lower than 1; p is an integer between 1 and 4; and r is higher than 0.

9. The method according to claim 8, wherein M3 is a divalent metal selected from Mg, Ca, Cu, Ni and any mixture thereof.

10. The method according to claim 9, wherein M3 is a divalent metal selected from Mg, Cu, Ni and any mixture thereof.

11. The method according to claim 8, wherein M4 is a trivalent metal selected from Al, Ni and any mixture thereof.

12. The method according to claim 11 wherein M4 is Al.

13. The method according to claim 8, wherein catalyst B comprises Cu and Ni.

14. The method according to claim 13, wherein the sum of the concentrations of Cu and Ni is between 0.2% to 10% by weight with respect to the total of catalyst B.

15. The method according to claim 8, wherein the molar ratio (Mg+Cu+Ni/Al) is between 1 and 6.

16. The method according to claim 1, wherein the weight ratio of catalysts A and B is between 1:10 to 10:1.

17. The method according to claim 16, wherein the proportion of catalysts A and B is 1:1.

18. The method according to any of claim 3, wherein the thermal decomposition of hydrotalcite $HT_A$ is performed by means of calcination under atmosphere of oxygen, nitrogen or any mixture thereof at a temperature ranging between 250° C. and 650° C., preferably between 350° C. and 550° C.

19. The method according to claim 8, wherein the thermal decomposition of hydrotalcite $HT_B$ is performed by means of calcination under atmosphere of oxygen, nitrogen or any mixture thereof at a temperature ranging between 250° C. and 650° C.

20. The method according to claim 3, wherein $Q_A$ is at least one anion selected from $CO_3^{2-}$, $HCO_3^-$, $O_2^-$ and $OH^-$.

21. The method according to claim 8, wherein $Q_B$ is at least one anion selected from $CO_3^{2-}$, $HCO_3^-$, $O_2^-$ and $OH^-$.

22. The method according to claim 1, the noble metal is added to the metal oxide of catalyst A by wet impregnation, incipient volume impregnation or deposition-precipitation.

23. The method according to claim 22, wherein, following the addition of the noble metal, there is a calcination step and a reduction step subsequent to the calcination.

24. The method according to claim 1, wherein the contact between ethanol, n-hexanol and catalysts A and B is performed at a pressure of up to 120 bar.

25. The method according to claim 1, wherein the contact between ethanol, n-hexanol and catalysts A and B is performed at a temperature ranging between 50° C. and 450° C.

26. The method according to claim 1, wherein the contact between ethanol, n-hexanol and catalysts A and B is performed under atmosphere of nitrogen, argon, hydrogen or any mixture thereof.

* * * * *

UNITED STATES PATENT AND TRADEMARK OFFICE
CERTIFICATE OF CORRECTION

PATENT NO. : 10,538,469 B2
APPLICATION NO. : 16/303387
DATED : January 21, 2020
INVENTOR(S) : Corma Canos et al.

It is certified that error appears in the above-identified patent and that said Letters Patent is hereby corrected as shown below:

In the Claims

Column 22, Claim 18, Line 37, "preferably between 350°C. and 550°C" should be deleted.

Signed and Sealed this
Fourteenth Day of April, 2020

Andrei Iancu
*Director of the United States Patent and Trademark Office*